US012796905B2

(12) United States Patent
Serfezi

(10) Patent No.: US 12,796,905 B2
(45) Date of Patent: Nov. 17, 2026

(54) MEDICAL DEVICE

(71) Applicant: Pirum Solmed Ltd, Limassol (CY)

(72) Inventor: Carmen-Roxana Serfezi, Empa (CY)

(73) Assignee: PIRUM SOLMED LTD, Limassol (CY)

( * ) Notice: Subject to any disclaimer, the term of this patent is extended or adjusted under 35 U.S.C. 154(b) by 150 days.

(21) Appl. No.: 18/881,858

(22) PCT Filed: Jul. 19, 2022

(86) PCT No.: PCT/CY2022/000001
§ 371 (c)(1),
(2) Date: Apr. 30, 2025

(87) PCT Pub. No.: WO2024/017424
PCT Pub. Date: Jan. 25, 2024

(65) Prior Publication Data
US 2025/0235092 A1 Jul. 24, 2025

(51) Int. Cl.
*A61B 1/31* (2006.01)
*A61B 1/00* (2006.01)

(52) U.S. Cl.
CPC ............ *A61B 1/31* (2013.01); *A61B 1/00066* (2013.01); *A61B 1/0008* (2013.01);
(Continued)

(58) Field of Classification Search
CPC .......... A45B 2009/007; A61B 1/00135; A61B 1/303; A61B 1/31; A61B 1/32;
(Continued)

(56) References Cited

U.S. PATENT DOCUMENTS 3,373,736 A * 3/1968 Fiore .................... A61B 1/0676 600/179
D384,412 S 9/1997 Mainiero
(Continued)

FOREIGN PATENT DOCUMENTS

EP 2308367 A1 4/2011

OTHER PUBLICATIONS

International Search Report, European Patent Office, Feb. 6, 2023.
Written Opinion ISA, European Patent Office, Feb. 6, 2023.

*Primary Examiner* — Michael J Carey
*Assistant Examiner* — Stephen Floyd London
(74) *Attorney, Agent, or Firm* — Bay State IP, LLC

(57) ABSTRACT

An anoscope (1) is formed by the intervention unit (2) and the control unit (3), which function as a single system by means of the insertion of unit 1 into unit (2) slidingly and pivotally. An interface and height-adjustable mechanism permits to adjust the axial distance of the multidimensional intervention unit aperture (5) from the control unit base (12). The mechanism is made of an alignment button (9), located on the external wall of the intervention unit (2), designed to engage with the interface and height-adjusting structures located on the internal wall of the transparent core body of the control unit (3) formed by a vertical alignment track (14) with three holes (10) indicating the access points for the intervention unit (2) to the three alignment grooves (18) extending on the internal surface of the wall of the control unit (3), along the whole circumference.

8 Claims, 3 Drawing Sheets

(52) U.S. Cl.
CPC ...... *A61B 1/00128* (2013.01); *A61B 1/00148* (2022.02); *A61B 1/00154* (2013.01)

(58) Field of Classification Search
CPC .. A61B 2017/00991; A61B 2017/3443; A61B 2017/345; A61B 2017/3452; A61B 2017/347; A61H 2201/0192; A61M 2025/0175; F16B 7/105
USPC ........................................... 403/109.3, 109.4
See application file for complete search history.

(56) References Cited

U.S. PATENT DOCUMENTS 6,079,894 A * 6/2000 Obitts ...................... A61H 3/02 403/109.2
6,142,931 A * 11/2000 Kaji ................... A61B 17/3421 600/105
6,142,933 A 11/2000 Longo et al.
10,980,561 B1 * 4/2021 Fahmy ................... A61B 18/04
2004/0133197 A1 * 7/2004 Utley ................. A61B 18/1477 606/41
2006/0009797 A1 1/2006 Armstrong
2008/0228213 A1 * 9/2008 Blakeney ........... A61B 17/3421 606/185
2008/0319269 A1 * 12/2008 Longo ................... A61M 29/00 600/235
2009/0005647 A1 1/2009 Bozdag
2009/0131881 A1 * 5/2009 Frisella, Jr. ........ A61B 17/3421 604/264
2009/0209813 A1 * 8/2009 Lubowski ................ A61B 1/31 600/156
2019/0059941 A1 * 2/2019 Cohen ................ A61B 17/3423
2020/0337722 A1 * 10/2020 Charles ................. A61F 9/0008
2020/0360048 A1 * 11/2020 White ................ A61B 1/00045
2021/0228198 A1 * 7/2021 LaPierre ............ A61B 17/3421

* cited by examiner

MEDICAL DEVICE

CROSS REFERENCE TO RELATED APPLICATION

This application is for entry into the U.S. National Phase from which priority is claimed under all applicable sections of Title 35 of the United States Code including, but not limited to, Sections 120, 363, and 365(c) to International Application No. PCT/CY2022/000001 filed on Jul. 19, 2022, the contents of which are incorporated by reference herein in its entirety as part of the present application.

FIELD OF THE INVENTION

The present invention relates to the field of medical devices, in particular to an anoscope for managing anorectal disease minimally invasive.

STATE OF THE ART

An anoscope is a medical instrument used mainly by proctologists, general or colon and rectal surgeons for gaining access to the anal canal and lower rectum for diagnostic and/or therapeutic purposes. It is generally a tubular device that is inserted into the anal canal, dilating the anatomic structures up to the lower rectum. It permits the clinicians to gain the best possible view of the anatomy of the lower rectum and the anal canal and facilitates easy access of the instruments required for therapeutic procedures.

One common application of anoscopes is the management of hemorrhoidal disease with either a minimally invasive non-excisional procedure (1st or 2nd line treatment) or an intervention reserved for severe cases that necessitates resection or excision (3rd line treatment).

Hemorrhoids are cushion-like clusters of an arteriovenous network and elastic connective tissue located beneath the mucous membranes lining the lowest part of the rectum and the anus. Their physiologic role is to protect the anal sphincter muscles, they help maintain faecal continence and influence the resting pressure of the anal canal. Hemorrhoidal disease, also called symptomatic hemorrhoids, is a clinical condition when those cushion-like clusters become swollen, inflamed, and generate symptoms. Constipation and constant straining during evacuation are causing congestion of the anal cushions, weakening their supporting structures, and leading ultimately to hemorrhoidal prolapse.

Symptomatic hemorrhoids are differentiated by their position vis-à-vis the dentate line. Those originating from the superior hemorrhoidal plexus, occur above the dentate line and are called internal hemorrhoids. External hemorrhoids originate from the inferior hemorrhoidal plexus, visible next to the anus.

The hemorrhoidal disease develops progressively through several stages, leading to vascular and muscle coordination dysfunction, and the prolapsing of anorectal structures.

Anoscopes are basically tubiform structures which are open at the proximal end (the extremity proximal to the medic or surgeon) and contain an opening at the distal end, in the sidewall or on both. Commercially available anoscopes are either made of metal or metal alloy, referred to as durable versions, or are made of a synthetic material, known as single use or disposable anoscopes, e.g. like in the anoscope shown in FIG. 1. However, such an anoscope has some drawbacks like not providing optimal conditions if the surgeon wants to deliver mucopexy and arterial ligation along multiple columns (essential to all techniques of the 2nd treatment line) and maintaining consistently throughout the procedure the same height of the device, because it lacks a height-adjustable feature. Furthermore, it requires hand-holding assistance during the procedure increasing unnecessarily the number of OR personnel required for the intervention. The geometry of the opening in the sidewall of this anoscope does not provide the surgeon with optimal visual conditions upon the anatomy in the region of interest and might hinder the surgeon in manipulating the needle during suturing. Additionally to the above mentioned disadvantages of the state of the art, one cannot disregard today's requirements of key stakeholder groups (e.g. medical services providers, patients, health insurance companies) and the challenges associated with various therapeutic measures and the devices involved in managing symptomatic internal hemorrhoids: patient safety, risks associated with excisional techniques, duration of hospitalization and postoperative recovery, limited clinical applications and learning curve—time required to achieve proficiency stage, in particular associated with complex equipment like Doppler-guided systems, the overall costs per procedure.

SUMMARY OF THE INVENTION

It is therefore the main purpose of the invention to provide a medical device designed for accessing the anal canal and lower rectum of a human being to overcome the above mentioned drawbacks and challenges that, in conformity to claim 1, comprises an intervention unit of cylindrical elongated shape having a first length and a control unit of cylindrical elongated shape having first distal and proximal open extremities and having a second length shorter than the first length, the intervention unit and the control unit are separate components and define a common longitudinal axis, the intervention unit is axially placed inside the control unit and is able to slide with respect to the control unit inside the control unit in a direction parallel to the common longitudinal axis and in a pivotal direction around the common longitudinal axis, the intervention unit has second distal and proximal extremities wherein the second distal extremity is closed by a rounded top and the second proximal extremity is open and a first main body intermediate to the distal and the proximal extremities has an aperture on a lateral wall near to the distal extremity designed for allowing viewing and accessing selectively anatomic structures of the lower rectum and anal canal, a fixing mechanism capable of blocking and unblocking longitudinal axial sliding and pivotal circumferential sliding between the intervention unit and the control unit in several axial and angular positions of the intervention unit in respect of the control unit.

Thanks to the specified features the anoscope of the invention enables surgeons to deliver transanal minimally invasive non-excisional procedures. The anoscope is formed by two distinct parts, defined as the intervention unit and the control unit, which together function as a single system due to their interfacing capability.

An interface and height-adjustable mechanism is housed by the transparent core body of the control unit, which allows the surgeons to adapt the height of the anoscope to overcome the anatomic differences due to the patient's physique or nature by facilitating a smooth alignment of the intervention unit at three levels (low, medium, high) as shown by the FIGS. 2, 3, 4 with the anatomic structures to be accessed selectively during the intervention. The multi-dimensional design of the intervention aperture of the intervention unit has dedicated fields for performing selectively arterial ligation using the section of the intervention aperture with a wide opening along the transversal direction to the longitudinal axis and mucopexy using the section of the intervention aperture with the longer dimension in the direction of the longitudinal axis of the anoscope.

BRIEF DESCRIPTION OF THE DRAWINGS

Further aspects and advantages of an anoscope according to this invention will become apparent from the following detailed description of preferred embodiments thereof, with reference to the accompanying figures, where.

Same reference numerals in different figures refer to the same component.

DESCRIPTION OF PREFERRED EMBODIMENTS OF THE INVENTION

Figure 1:
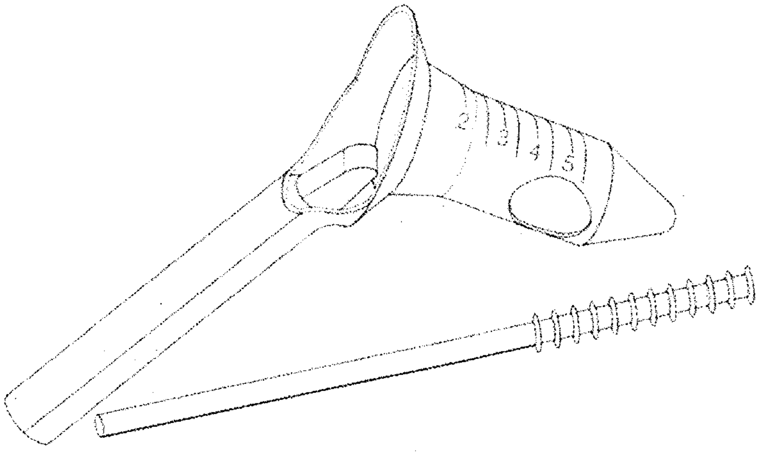
FIG. 1: shows an anoscope according to the state of the art.

The invention will be better understood by reading hereafter the description of preferred embodiments of the medical device, also defined as anoscope, according to the invention. With reference to the figures, the anoscope of FIG. 2, globally indicated with reference numeral 1, and of a substantially cylindrical shape with its longitudinal axis parallel to the axis Y, of the orthogonal coordinates system X, Y, Z, is a height-adjustable device comprising two different components: the first component is an intervention unit 2 and the second component is a control unit 3. The components 2 and 3 of the anoscope 1 are designed to function as a system centered on their interfacing capability provided by the alignment button 9 located on the external surface of the wall, in the proximal portion of the intervention unit 2 along a generatrix of the cylinder lying on the plane YZ, and a height-adjusting structure located on the internal surface of the wall of the control unit 3.

The height adjusting structure is formed by a longitudinal alignment track 14, located on the internal surface of the wall of the control unit 3, along a generatrix lying on the plane YZ, that permits the insertion of the intervention unit 2 into the control unit 3 and an axial shifting of the intervention unit 2 within the control unit 3.

The control unit 3 is provided also with three holes 10 made on its wall, which are aligned along the alignment track 14, and indicate the access points for the intervention unit 2 to the three alignment grooves 18 extending on the internal surface of the wall of the control unit 3, along the whole circumference for 360°. The alignment grooves 18 allow a pivotal clockwise and anticlockwise movement around the longitudinal axis of the intervention unit 2 inside the control unit 3 and have the function of guides for the button 9 in the three positioning levels of the anoscope: low, medium and high levels.

Figure 2:
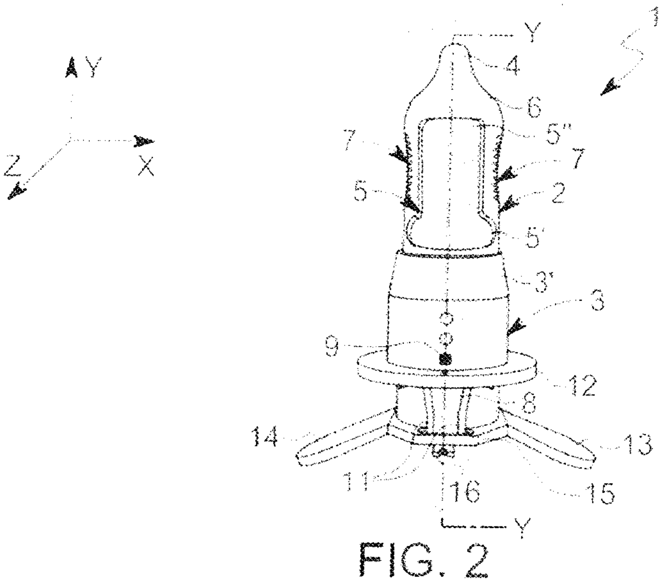
FIG. 2: shows an axonometric frontal view of the anoscope of the invention in its assembled configuration for use, with the intervention unit inserted into the control unit and set at level low.
Figure 3:
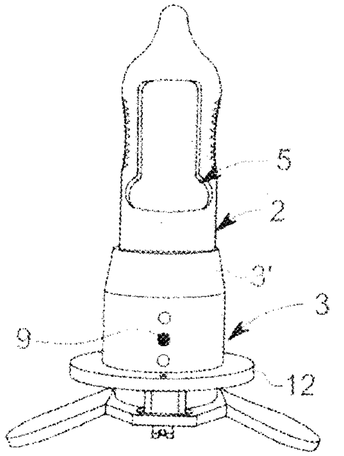
FIG. 3: shows the anoscope of FIG. 2 assembled for use with the intervention unit inserted into the control unit and set at level medium.
Figure 4:
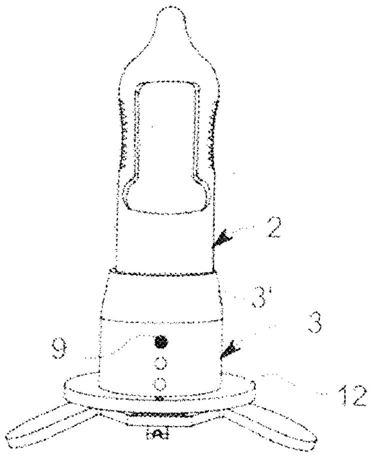
FIG. 4: shows the anoscope of FIG. 2 assembled for use with the intervention unit inserted into the control unit and set at level high.
Figure 5:
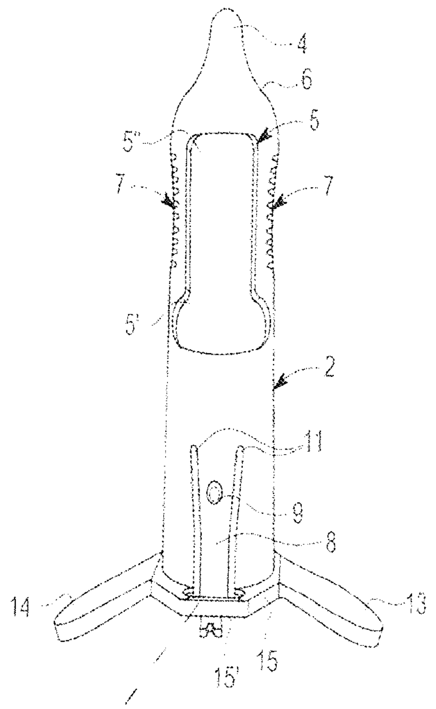
FIG. 5: shows an axonometric frontal view of the intervention unit, the first component of the anoscope of FIG. 2, FIG. 6: shows an enlarged view of the frontal bottom part of the intervention unit of FIG. 5, FIG. 7: shows an axonometric lateral view of the intervention unit of the anoscope of FIG. 5, FIG. 8: shows an axonometric frontal view of the control unit, the second component of the anoscope of FIG. 2, FIG. 9: shows an axonometric view in axial direction of the height adjustable structure located on the internal wall of the control unit of FIG. 8.

The anoscope 1 in its assembled form for use shown in FIG. 2 has the intervention unit 2 fixed at level low, whereas FIG. 3 and FIG. 4 display the anoscope 1 assembled for use respectively at levels medium and high.

The intervention unit 2 has a substantially cylindrical shape, is axially elongated and has a closed top 4 at its distal extremity which is dome-shaped and is joined to the main body of the intervention unit 2 over a double curved surface 6. This surface 6, when considering its cross section lying on an axial plane, has a rate of change of the angle through which the tangent to the curve turns in moving along the curve going from a positive value to a negative value. The top 4, also defined as anatomical tip, permits an easy insertion into the anal canal and a smooth lifting of the prolapsed anatomic structures.

In the distal portion of the wall of the intervention unit 2, immediately below the anatomical tip 4, there is provided a multidimensional intervention aperture 5 framing the dedicated fields through which the surgeon performs selectively arterial ligation and mucopexy. Arterial ligation can be performed through the first section 5', which is shaped as a wider opening extending along the wall of the intervention unit 2 with its longer dimension extending in the circumferential direction of the intervention unit 2. Mucopexy can be performed through the second section 5" of the intervention aperture 5 of substantially rectangular shape with its greater dimension extending in the direction of the longitudinal axis Y of the intervention unit 2.

Figure 6:
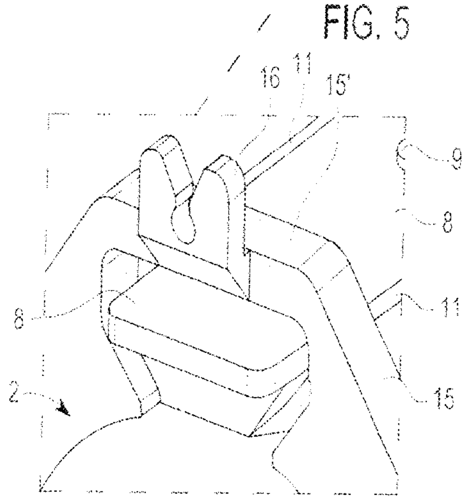
Figure 7:
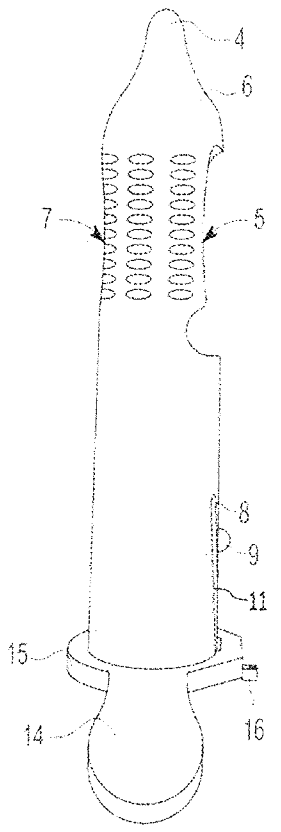
Figure 8:
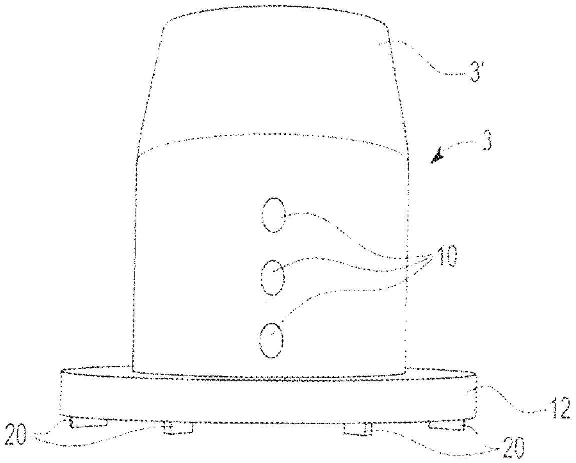
Figure 9:
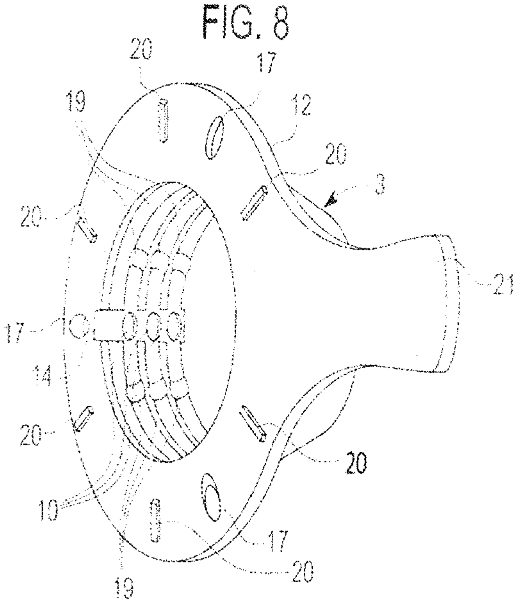
Figure 10:
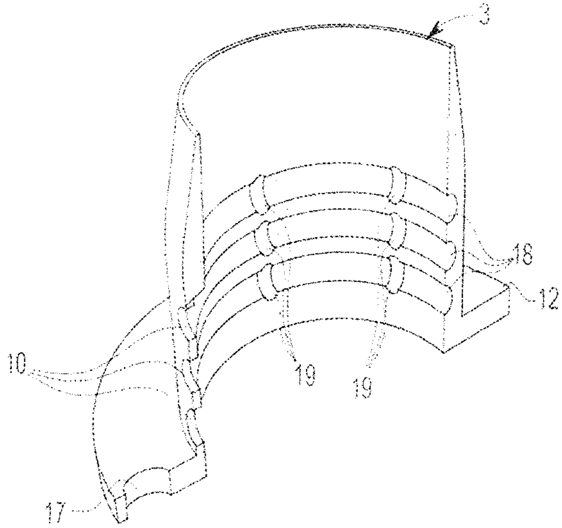
FIG. 10: shows an enlarged cross-section view on an axial plane of the control unit of FIG. 8.

Two pressure relief slits 11 are advantageously located on the frontal wall of the proximal part of the intervention unit 2 to the left and to the right of the alignment button 9 in respect of the longitudinal axis of the intervention unit 2. These slits 11 are provided to enhance the elasticity and the biasing capacity of the wall of the intervention unit 2 in the portion 8 defined between the pressure relief slits 11, as this zone is not fixed to the base 15 of the intervention unit, as shown in the enlargement of FIG. 6. The portion 8 of wall between the two slits 11 has thus the form of a flexible biasing bar 8 enabling the surgeon to easily lock and unlock the alignment button 9 during the intervention. By unlocking the alignment button 9 for executing longitudinal shifting of the intervention unit 2 along the alignment track 14 of the control unit 3 the surgeon can choose, in consideration of the patient's anatomic characteristics, the most appropriate level, e.g. low, medium or high, as shown respectively in FIGS. 2, 3 and 4, for positioning correctly the intervention aperture 5 in relation to the dentate line that serves usually as an anatomic reference point. The core body of the control unit 3 is transparent and thus provides the surgeon with optimal visual conditions to locate the anatomic reference point.

However, if it is more appropriate to the needs of patients, in consideration of their anatomic structure, as an alternative the number of holes 10 foreseen in the control unit 3 can be more than three, to allow for a higher number of axial positions between the intervention unit 2 and the control unit 3.

The same action of locking and unlocking is carried out by the surgeon for allowing a change in the angular orientation of the intervention aperture 5, unblocking the button 9 by making a slight pressure on the portion 8 of wall more flexible and sliding the button 9 circumferentially in the alignment groove 18 of interest until the intervention unit 1 reaches the desired angular position in respect to the control unit 2 and to the patient's body.

By changing the angular orientation of the intervention aperture 5, the surgeon can access selectively the quadrants of interest as required by the procedure sequence. In the pivoting movement of intervention unit in the control unit the alignment button 9 can engage one of several, preferably but not exclusively six, alignment cavities 19, placed at 60° distance one to each other along the circumference. In this manner the two units 2 and 3 maintain constant and securely their relative angular orientation and the direction of the intervention aperture 5, in the position selected by the surgeon. Advantageously, a thread support 16, shown in the enlarged detail of FIG. 6, is incorporated in the frontal section of the base 15 of the intervention unit 2 where it forms a bridge 15' over the wall 8 of the intervention unit 2 between the pressure relief slits 11.

The thread support 16 helps the surgeon to keep the proximal end of the thread out of his/her visual field when it is not required or for tightening the thread, as desired by the surgeon to carry out the suturing under optimal conditions.

Advantageously, the surface of the external wall of the distal portion of the intervention unit 2 is patterned like sharkskin 7, in the wall section behind the intervention aperture.

The control unit 3 has a transparent core body of cylindric shape, a frusto-conical distal section 3', a base 12 formed like a ring-type structure and has advantageously a handle 21 extending radially from the base 12 to have a better grip on the control unit 3. Three holes 17, preferably, though not necessarily, of oval shape, are provided on the base 12, for fixing the control unit 3 on the patient's body by means of sutures to prevent accidental movement during the intervention and enabling the surgeon to perform the procedure autonomously.

Six orientation marks 20 at the bottom of the base 12 are an orientation aid for the surgeon, indicating the location where the alignment button 9 of the intervention unit 2 meets the alignment cavities 19 distributed evenly along each of the three alignment grooves 18.

Advantageously, two handles 13 and 14 are fixed at both sides of the base 15 of the intervention unit 2 and are oriented at an angle of slight magnitude away from the patient's posterior.

The peculiar features of the anoscope 1 of the invention as described above offer several advantages over other known anoscopes in addition to the advantages already explained above:

- the anatomical tip 4 having a double-curved design and a closed top provides optimal visualization upon the area in which the intervention is performed by preventing access of tissue or stool into the anoscope inner space. It also facilitates a smooth physical lifting of prolapsed tissue during the insertion of the anoscope 1, and provides a support platform for the anatomic structures surrounding the distal part of the intervention unit 2 during the surgical or medical intervention;
- the multidimensional intervention aperture 5 on the frontal wall of the anoscope frames the fields 5' and 5" through which the clinician performs selectively arterial ligation and/or mucopexy, and provides the surgeon with optimized conditions for manipulating the instruments used during the intervention enhancing the quality of the suture along each column while performing superficial and/or deep passages with the needle;
- the surface patterned like sharkskin 7 enhances the support and facilitates an even distribution of the prolapsed tissue that is in direct contact with the wall of the intervention unit 2 in the respective area;
- the two handles 13, 14 allow the surgeon to easily grab and hold the intervention unit 2 while manipulating the anoscope during the procedure;
- the frusto-conical distal section 3' of the control unit 3 fits like a sleeve over the intervention unit anatomic tip 4, and provides stability during the insertion of the control unit 3 in the anal canal;
- the positioning and aligning structure allows the surgeon to easily select the height of the positioning of the intervention aperture 5 and its angular position, giving to the anoscope a broader field of use in performing interventions.
- the height-adjustability of the anoscope 1 permits the clinician to overcome anatomic differences caused by the patient's physique or nature and facilitates a minimally invasive management of anorectal disease under optimal conditions while delivering non-excisional therapeutic solutions;
- the transparent body of the control unit 3 allows a clinician to see the dentate line and use it as an anatomic reference point in determining the appropriate level, above the dentate line, at which the intervention shall be performed;
- the provision of the anatomical tip 4 formed by a double-curved closed top enables a smooth physical lifting of the prolapsed tissue during the insertion of the device and provides a support platform during the intervention for the anatomic structures that surround the distal extremity of the intervention unit 2;
- the two pressure relief slits 11 in the intervention unit 2 enhance the elasticity of the device's wall and to enable the clinician to navigate safely and easily the height-adjustable structure inside the control unit 3 by actuating the alignment button 9 of the intervention unit 2;
- the feature 16, used as thread support, enables the surgeon to keep the lower end of the thread out of the visual field when it is not required or to tighten the thread, as desired by the surgeon to carry out suturing under optimal conditions.

Furthermore, other advantages of the device according to the invention are to maximize patient safety, to provide an opportunity of reducing the overall cost of the procedure compared to the use of Doppler-guided techniques, to minimize surgeon's dependency on OR assistance.

The anoscope of the invention also enhances clinical effectiveness of the therapeutic measures on high-risk patients (e.g. patients under anticoagulant therapy, comorbidities) or patients requiring revisional procedures in the event that third line treatment techniques failed delivering the expected results.

The invention has been described in all details as being a medical device for therapeutic procedures on humans. It is readily apparent to the skilled person that it can also be applied to veterinary procedures. Although the anoscope has been disclosed as a device for single use and in this case, it is made of synthetic resins, it is clear without departing from the scope of the invention that it can be made of a more durable material, e.g. metal or other appropriate material that can be re-sterilised to be used several times.

The invention claimed is:

1. A medical device (1) designed for accessing the anal canal and lower rectum of a human being, comprising an intervention unit (2) of cylindrical elongated shape having a first length and a control unit (3) of cylindrical elongated shape having first distal and proximal open extremities and having a second length shorter than the first length, wherein the intervention unit (2) and the control unit (3) are separate components and define a common longitudinal axis Y, wherein the intervention unit (2) is axially placed inside the control unit (3) and is able to slide with respect to the control unit (3) inside the control unit (3) in a direction parallel to the common longitudinal axis Y and in a pivotal direction around the common longitudinal axis Y, wherein the intervention unit (2) has second distal and proximal extremities, wherein the second distal extremity is closed by a rounded top (4) and the second proximal extremity is open, a first main body intermediate to the second distal and proximal extremities, a multidimensional aperture (5) laterally on a wall near to the distal extremity (4) designed for allowing viewing and accessing selectively anatomic structures of the lower rectum and anal canal, characterised in that the medical device has a fixing mechanism (8, 9, 10, 11, 19) capable of blocking and unblocking the sliding in the direction parallel to the common longitudinal axis Y and in the pivotal direction around the common longitudinal axis Y between the intervention unit (2) and the control unit (3) in several axial and angular positions of the intervention unit (2) in respect of the control unit (3), wherein the fixing mechanism is a height adjustable mechanism comprising a button (9) placed on a flexible bar (8) of an external surface of the first main body of the intervention unit (2) entering in a hole of a plurality of holes (10) made on the control unit (3) and aligned along a vertical alignment track (14) at a distance to each other and comprising a plurality of circumferential grooves (18) located in an internal surface of the control unit (3).

2. The medical device according to claim 1, wherein the rounded top (4) is joined to the first main body of the intervention unit (2) by a surface (6) having a double curvature of opposite signs.

3. The medical device according to claim 1, wherein the control unit (3) is made, at least partly of transparent material.

4. The medical device according to claim 1, wherein the aperture (5) is constituted by two areas (5', 5") of different perimeters and shapes.

5. The medical device according to claim 1, wherein the intervention unit (2) has a pair of slits (11) on the wall, whereby the flexible bar (8) is created.

6. The medical device according to claim 1, wherein on a base (15) of the intervention unit (2) there is fixed a support (16) for a suture thread.

7. The medical device according to claim 1, wherein the control unit (3) has a base (12) with holes (17) for allowing suturing the medical device to the patient's posterior.

8. The medical device according to claim 1 wherein the medical device is a height-adjustable anoscope.

* * * * *